United States Patent [19]
Campbell et al.

[11] Patent Number: 5,413,910
[45] Date of Patent: * May 9, 1995

[54] MEASURING NON-DYSTROPHIN PROTEINS AND DIAGNOSING MUSCULAR DYSTROPHY

[75] Inventors: Kevin P. Campbell; James M. Ervasti; Kay Ohlendieck, all of Iowa City, Iowa; Mitchell G. Gaver, Cockeysville, Md.; Steven D. Kahl, Iowa City, Iowa

[73] Assignee: University of Iowa Research Foundation, Iowa City, Iowa

[*] Notice: The portion of the term of this patent subsequent to Feb. 16, 2010 has been disclaimed.

[21] Appl. No.: 958,015

[22] Filed: Oct. 7, 1992

Related U.S. Application Data

[63] Continuation of Ser. No. 527,583, May 23, 1990, Pat. No. 5,187,063.

[51] Int. Cl.⁶ .............................................. G01N 33/567
[52] U.S. Cl. ................................. 435/721; 435/240.27; 436/63; 436/518; 436/811; 530/388.2; 530/389.1
[58] Field of Search .......................... 530/389.1, 388.2; 435/7.21, 240.27; 436/63, 518, 547, 548, 811

[56] References Cited

U.S. PATENT DOCUMENTS 4,912,202  3/1990  Campbell et al. ................. 530/388.2
5,187,063  2/1993  Campbell et al. .................. 435/7.21

FOREIGN PATENT DOCUMENTS 0331514  9/1989  European Pat. Off.
WO89/06286  7/1989  WIPO.

OTHER PUBLICATIONS

Hoffman, E. P., et al., "Dystrophin: The Protein Product of the Duchenne Muscular Dystrophy Locus," Cell, 51: 919-928 (1987).
Maurer et al., Proteins and Polypeptides as Antigens, Methods in Enzymology 70: 49-69, 1980.
Knudson, C. M., et al., "Evidence for the Association of Dystrophin with the Transverse Tubular System in Skeletal Muscle," J. of Biol. Chem., 263(17): 8480-8484.
Hoffman, E. P., et al., "Characterization of Dystrophin in Muscle-Biopsy Specimens from Patients with Duchenne's or Becker's Muscular Dystrophy," N.E. J. Med., 318(21): 1363-1368 (1988).
Zubrzycka-Gaarn, E. E., et al., "The Duchenne Muscular Dystrophy Gene Product is Localized in Sarcolemma of Human Skeletal Muscle," Nature, 333: 466-469 (1988).
Arahata, K., et al., "Immunostaining of Skeletal and Cardia Muscle Surface Membrane with Antibody against Duchenne Muscular Dystrophy Peptide," Nature, 333: 861-863 (1988).
Bonilla, E., et al., "Duchenne Muscular Dystrophy: Deficiency of Dystrophin at the Muscle Cell Surface," Cell, 54: 447-452 (1988).
Cooper, B. J., et al., "The Homologue of the Duchenne Locus is Effective in X-linked Muscular Dystrophy of Dogs," Nature, 334: 154-156 (1988).
Campbell, K. P., and Kahl, S. D., "Association of Dystrophin and an Integral Membrane Glycoprotein," Nature, 338: 259-262 (1989).
Ervasti, J. M. et al., "Deficiency of a Glycoprotein Component of the Dystrophin Complex in Dystrophic Muscle," Nature, 345: 315-319 (1990).
A. O. Jorgensen et al., "Identification of Novel Proteins Unique to Either Transverse Tubules (TS28) or the Sarcolemma (SL50) in Rabbit Skeletal Muscle," Journal of Cell Biology 110: 1173-1185 (1990).
Sevier et al., "Monoclonal Antibodies in Clinical Immunology," Clinical Chemistry 27(11): 1797-1806 (1981).

Primary Examiner—Esther M. Kepplinger
Assistant Examiner—Donna C. Wortman
Attorney, Agent, or Firm—Kevin M. Farrell

[57] ABSTRACT

The invention pertains to the dystrophin-glycoprotein complex of mammalian skeletal muscle and a method of isolating said complex. The components of the complex and methods of separating and isolating said components also pertain to the invention. In addition, the invention further relates to a method of diagnosing muscular dystrophy by detecting and quantifying the loss of a non-dystrophin component of the dystrophin-glycoprotein complex with said loss being indicative of muscular dystrophy.

7 Claims, 11 Drawing Sheets

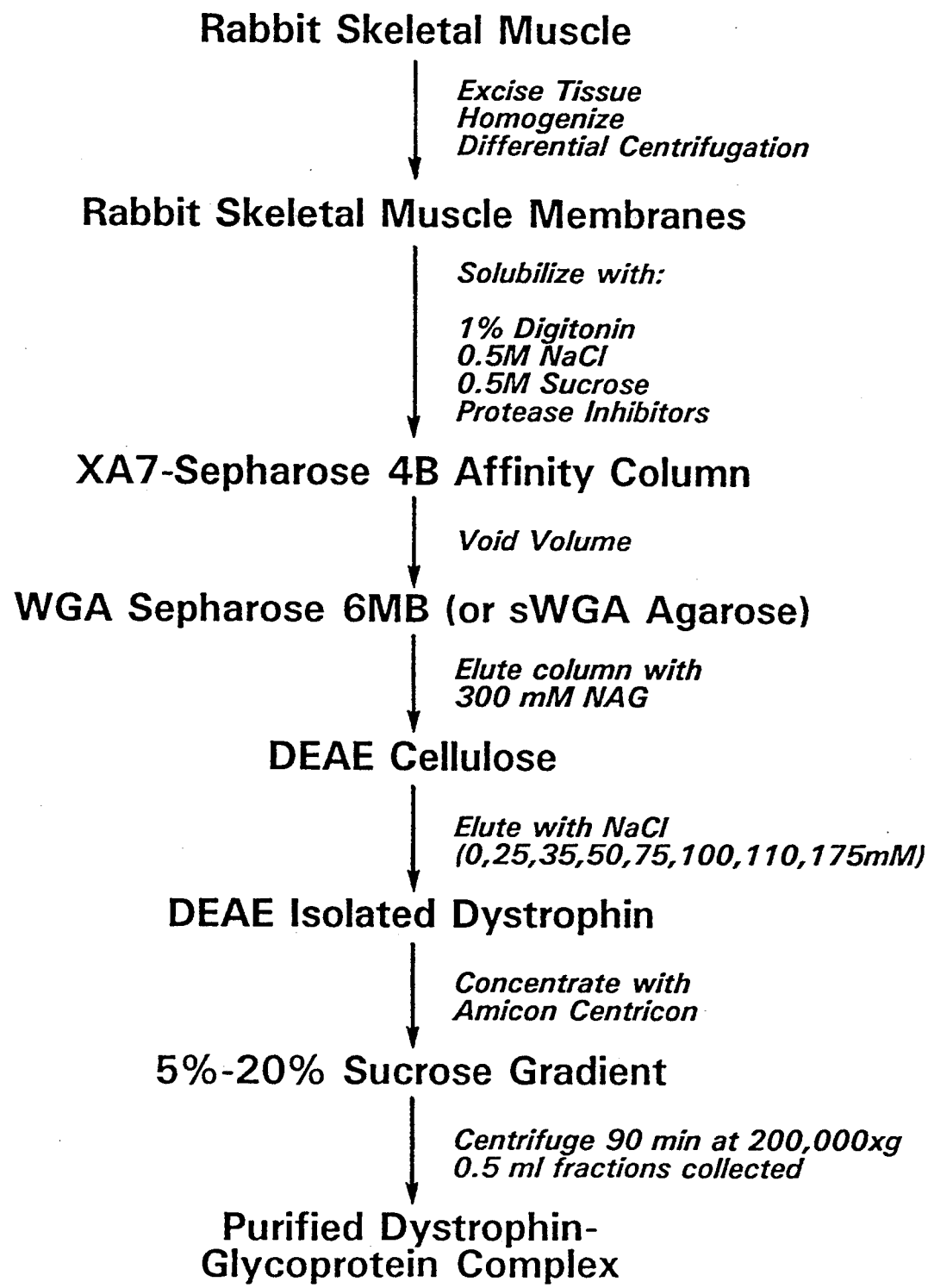

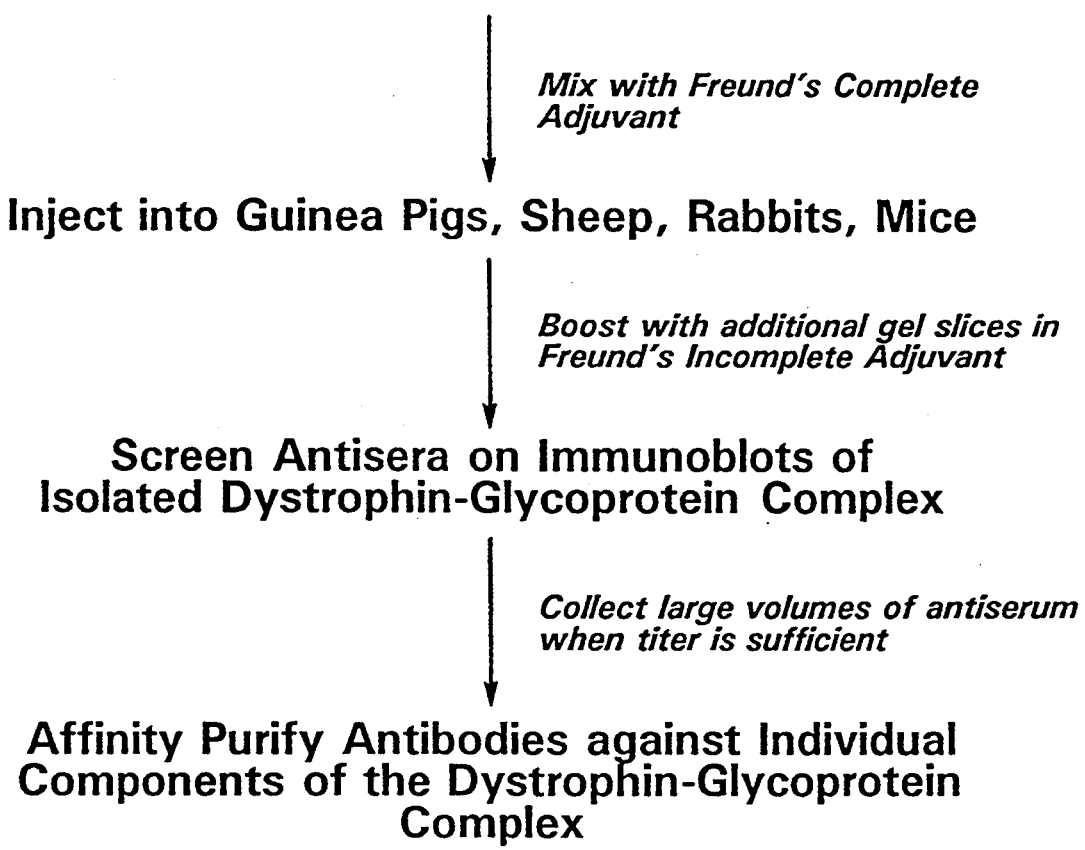

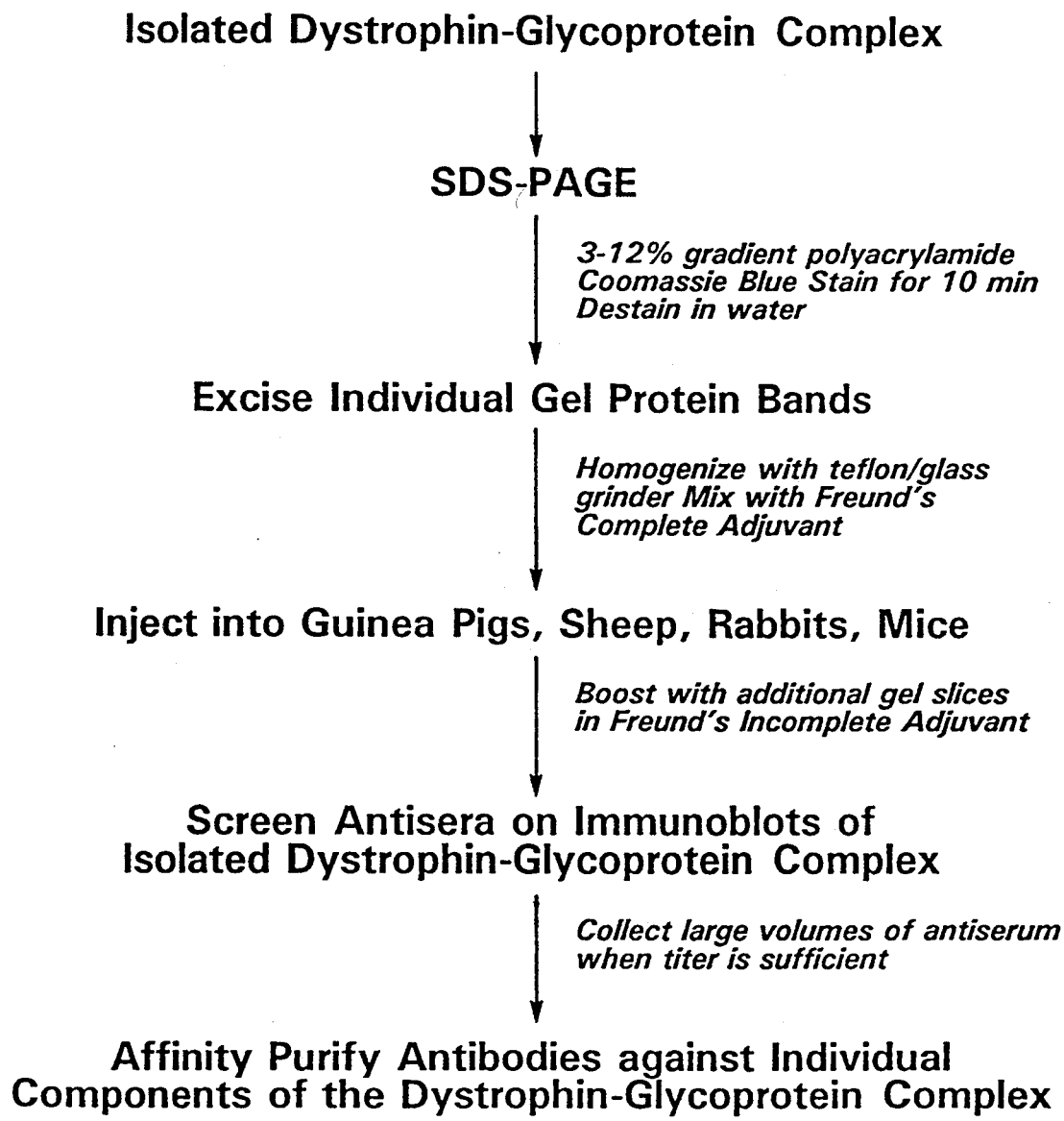

IVD3₁

$M_r$ (×10⁻³): 224, 109, 72, 46, 29

← 50GP

Fraction: 7 8 9 10 11 12 13 14 15 16 17

FIG. 4e

VIA4₁

$M_r$ (×10⁻³): 224, 109, 72, 46, 29

← 156GP

Fraction: 7 8 9 10 11 12 13 14 15 16 17

FIG. 4f

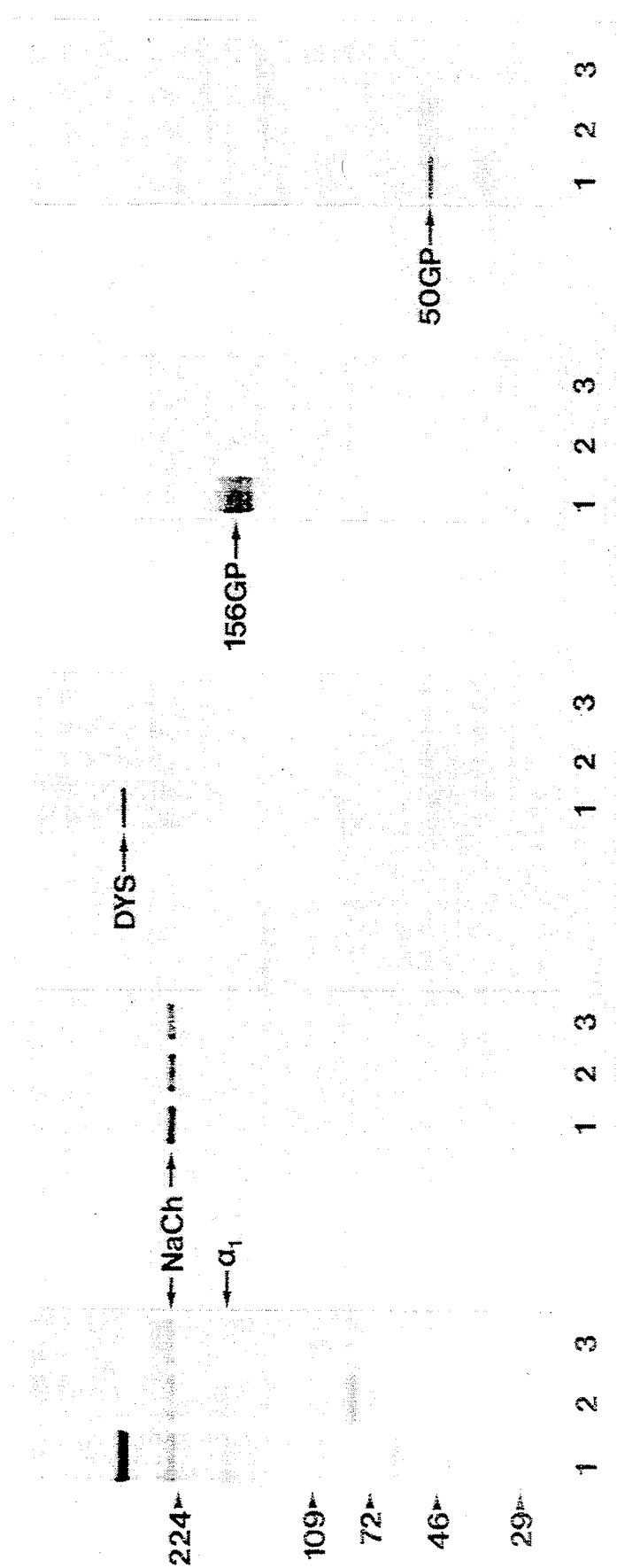

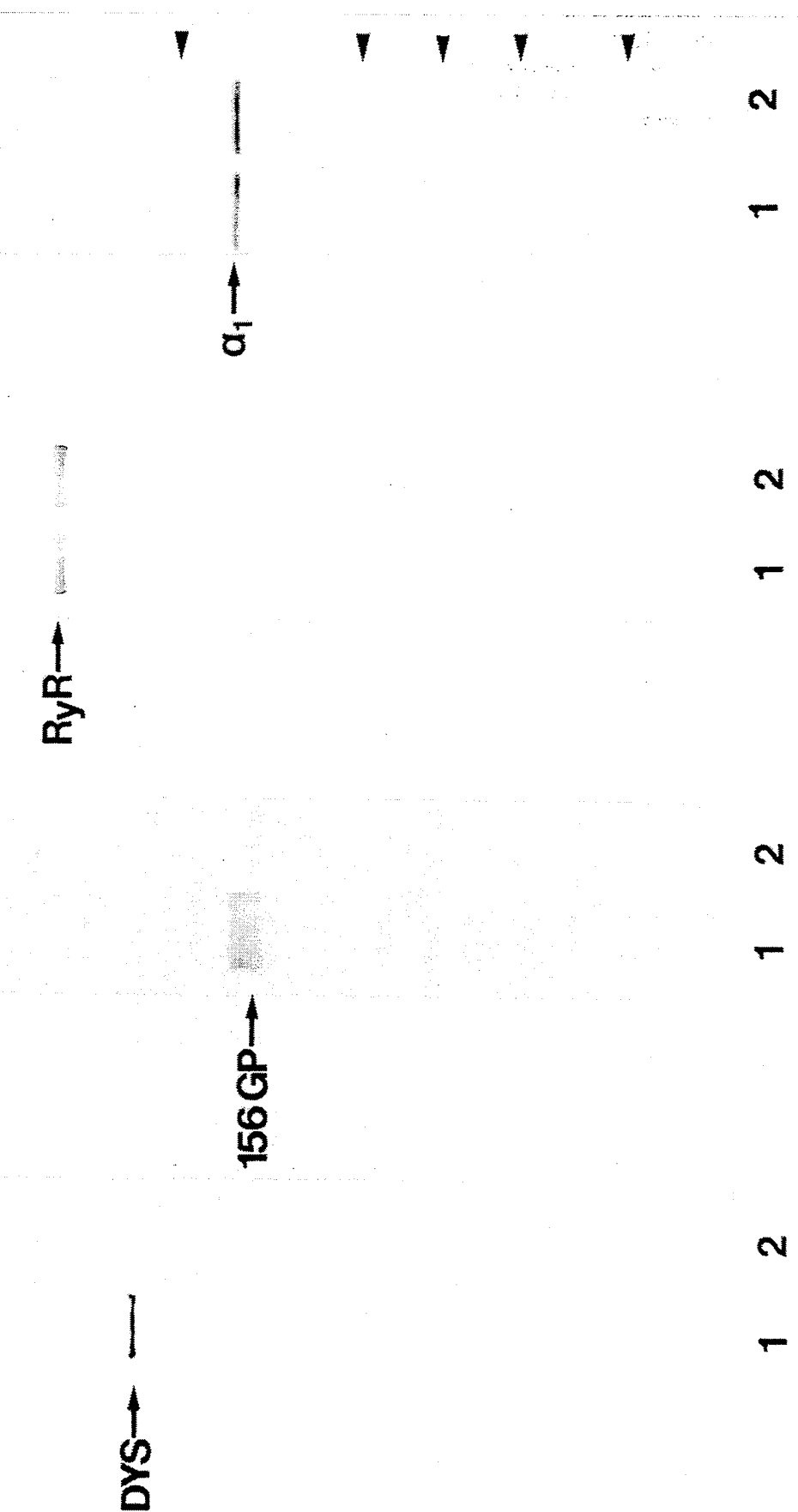

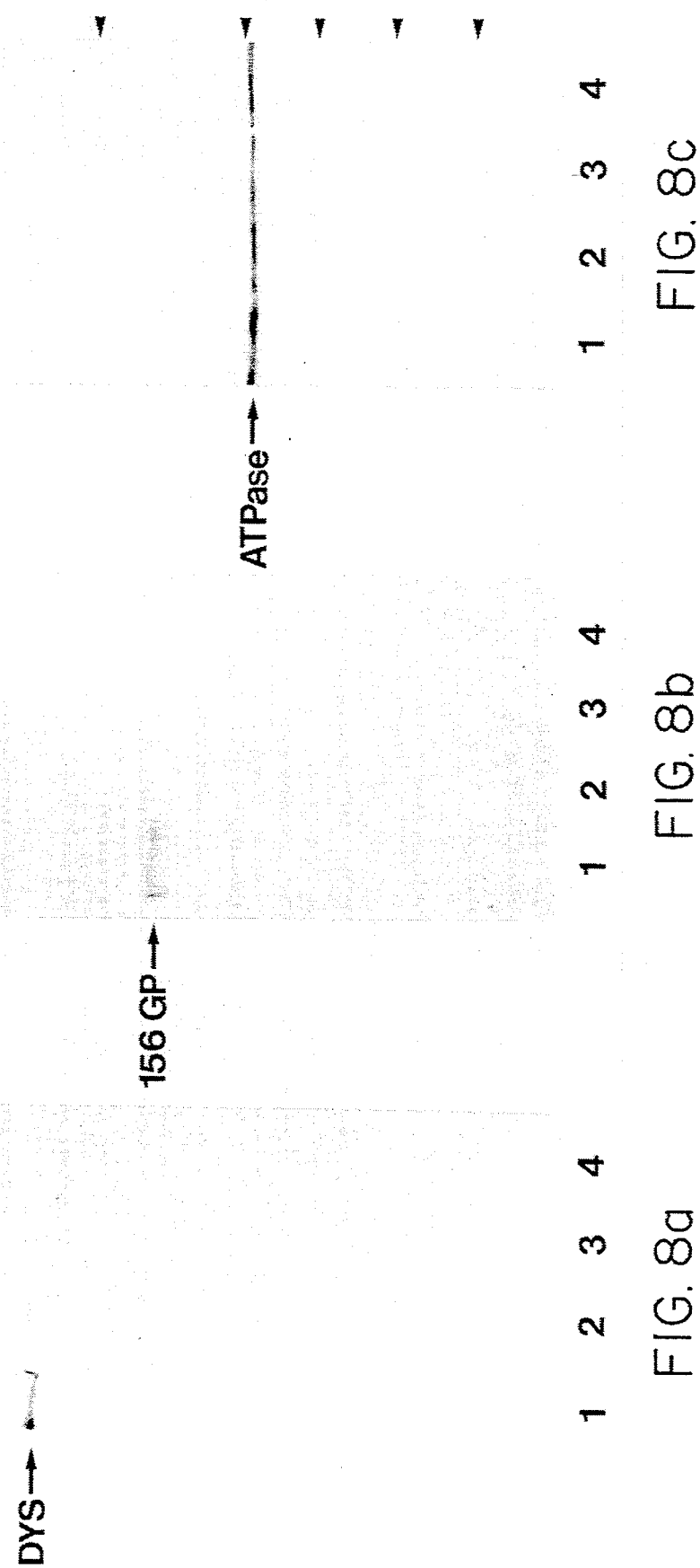

MEASURING NON-DYSTROPHIN PROTEINS AND DIAGNOSING MUSCULAR DYSTROPHY

This application is a continuation of application Ser. No. 07/527,583. U.S. Pat No. 5,187,063 filed on May 23, 1990.

BACKGROUND OF THE INVENTION

Muscular dystrophy refers to a group of genetically determined myopathies characterized by progressive atrophy or degeneration of increasing numbers of individual muscle cells. The structural changes observed histologically are essentially the same in the various types of muscular dystrophies. This may, perhaps, suggest a common etiology. However, the distribution of the affected muscles is quite distinctive. This, along with the mode of inheritance, forms the basis of the classification of these diseases. The muscular dystrophies are traditionally subdivided by the patterns of initial muscle involvement, which in turn correlates fairly well with the type of genetic transmission. The three major forms of muscular dystrophy are as follows: 1) Duchenne's Muscular Dystrophy which affects most skeletal muscle groups and is transmitted by an X-linked recessive gene; 2) Limb Girdle Muscular Dystrophy, affecting principally the pelvic and shoulder girdle muscles and is transmitted by an autosomal recessive gene; and 3) Facioscapulohumeral Muscular Dystrophy, involves the muscles of the face and shoulder girdle and is transmitted by an autosomal dominant gene.

Recently, the defective gene responsible for Duchenne's Muscular Dystrophy (DMD) has been located on the X-chromosome. The DMD gene encodes for a large molecular weight protein product, called dystrophin. This protein is localized to the sarcolemmal membrane of normal skeletal muscle, but is absent from the skeletal muscle of people with DMD, as well as dogs and mice with dystrophic muscle. A more benign form of this X-linked recessive disease is Becker's Muscular Dystrophy which is caused by an abnormal DMD gene which encodes an abnormal dystrophin protein. The exact function of dystrophin and the reasons why its absence or abnormal structure results in necrosis of dystrophic muscle fibers have not been determined. However, the amino acid sequence of dystrophin suggests that it is a membrane cytoskeletal protein.

The present technology for initial detection and diagnosis of Duchenne's or Becker's Muscular Dystrophy relies on the use of an immunological probe to identify the presence of dystrophin, the absence of dystrophin, or the abnormal molecular weight or content of dystrophin in human muscle biopsies. It is not uncommon for genetic diseases to involve the loss or abnormal synthesis of more than one component or protein. In the case of muscular dystrophy, proteins other than dystrophin may be involved which are translated from genes located on different chromosomes (X chromosomes and/or autosomal chromosomes), resulting in the different forms of muscular dystrophy. The identification of other potential proteins involved in muscular dystrophy and methods of quantifying these proteins would be immensely useful to clinicians for confirming diagnosis of Duchenne's and Becker's muscular dystrophy, as well as perhaps providing an initial diagnosis of other forms of muscular dystrophy. In addition, knowledge of the function of these proteins may lead to methods of predicting prognosis of disease progression and perhaps therapeutic treatments for patients with muscular dystrophy in all of its various forms.

SUMMARY OF THE INVENTION

The invention pertains to the dystrophin-glycoprotein complex of mammalian skeletal muscle and a method of isolating said complex. The invention also pertains to the non-dystrophin components of the dystrophin-glycoprotein complex of mammalian skeletal muscle and a method of separating and isolating said components. The components comprise a 156 kDa glycoprotein, a triplet of proteins with a molecular weight of 59 kDa, a 50 kDa glycoprotein, a 43 kDa glycoprotein and a 35 kDa glycoprotein.

The invention further pertains to a method of diagnosing muscular dystrophy by detecting and quantifying the loss of a non-dystrophin component of the dystrophin-glycoprotein complex of mammalian skeletal muscle with said loss being indicative of muscular dystrophy.

Monoclonal and polyclonal antibodies specific for the non-dystrophin components of the dystrophin-glycoprotein complex are particularly useful in the diagnostic method of this invention. For example, these antibodies can be labeled and used for binding to the non-dystrophin components, thereby allowing detection of said components. This detection can occur if the components are in isolated form or in natural form as linked to dystrophin in normal skeletal muscle.

The present invention is based, in part, on the discovery that dystrophin exists in the sarcolemmal membrane as a component of an oligomeric complex. Dystrophin is known to be greatly reduced in dystrophic muscle. The present invention utilizes newly discovered information in that a non-dystrophin component of the dystrophin glycoprotein complex is also markedly decreased. This invention offers a novel and alternative means of diagnosing Duchenne's and Becker's muscular dystrophy by detecting the loss of non-dystrophin components of the dystrophin-glycoprotein complex and may provide a means for diagnosing other forms of muscular dystrophy.

BRIEF DESCRIPTION OF THE DRAWINGS

FIG. 1 is a flow diagram of the steps comprising the preparation of the dystrophin-glycoprotein complex from mammalian skeletal muscle.

FIG. 2 is a flow diagram of the steps comprising the production of polyclonal antibodies to the dystrophin-glycoprotein complex.

FIG. 3 is flow diagram of the steps comprising the production of polyclonal antibodies to the non-dystrophin components of the dystrophin-glycoprotein complex.

FIG. 6 a, b, c, d and e depict the immunoadsorption of the dystrophin-glycoprotein complex with monoclonal antibodies XIXC2 and IVD3$_1$ and the immunological detection of the dihydropyridine receptor, the C-terminal decapeptide of dystrophin, the 156 kDa glycoprotein and the 50 kDa glycoprotein in respective column voids.

FIG. 7 a, b, c, d, depicts the immunoblot analysis of muscle membranes from control and dystrophic mice for the presence of the C-terminal decapeptide of dystrophin, the 156 kDa glycoprotein, the ryanodine receptor and the dihydropyridine receptor.

FIG. 8 a, b, and c depicts the immunoblot analysis of normal and dystrophic human muscle biopsies for the presence of dystrophin, the 156 kDa glycoprotein and the ($Ca^{2+}$, $Mg^{2+}$) ATPase

DETAILED DESCRIPTION OF THE INVENTION

Figure 4A:
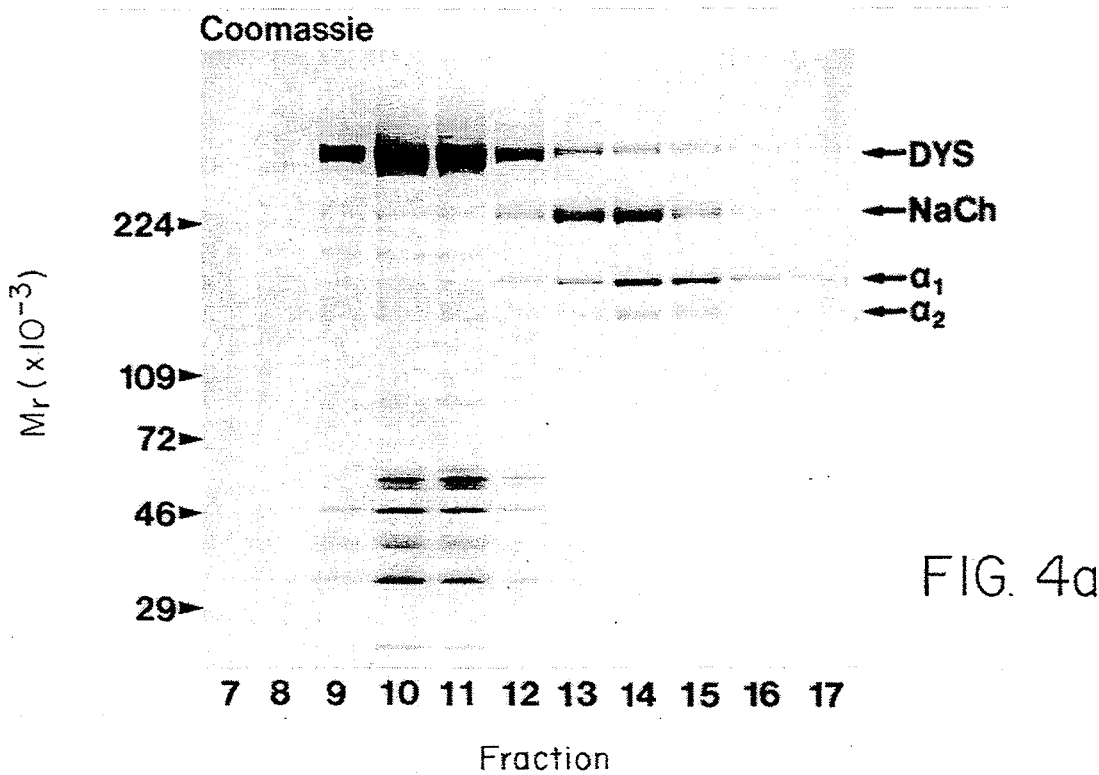
FIG. 4 a, b, c, d e, and f depict the sedimentation of the dystrophin-glycoprotein complex through 5% to 20% linear sucrose gradients and the staining of sucrose gradient fractions 7-17 for protein, WGA-binding proteins, the C-terminal decapeptide of dystrophin, dystrophin, the 50 kDa glycoprotein and the 156 kDa glycoprotein.

The techniques described herein are not limiting, but merely specific examples of techniques that can be employed in the isolation and diagnostic methods of this invention.

Dystrophin is a large molecular weight protein product of the defective gene responsible for Duchenne's Muscular Dystrophy. This invention is based, in part, on the discovery that dystrophin exists as a component of a large oligomeric complex in the sarcolemmal membrane of normal skeletal muscle. Proteins and glycoproteins comprise the other components of this complex which is hereforwith referred to as the dystrophin-glycoprotein complex. Specifically, the other components comprise a 156 kDa glycoprotein, a 50 kDa glycoprotein, a 43 kDa glycoprotein, a 35 kDa glycoprotein and a triplet of proteins of 59 kDa molecular weight. These components are referred to as the non-dystrophin components of the dystrophin-glycoprotein complex. At least one of the components of the dystrophin-glycoprotein complex is an integral membrane protein since 1.0% digitonin (detergent) is necessary to solubilize the complex.

The dystrophin-glycoprotein complex can be isolated from detergent solubilized skeletal muscle membranes using affinity chromatography and density gradient ultracentrifugation as illustrated in FIG. 1. Lectins are proteins or glycoproteins which bind certain sugars or oligosaccharides. This property can be used to pick out certain glycoproteins from a complex mixture and is extremely useful as a general approach to the purification of membrane proteins, many of which are glycosylated. In the present invention, the linked components of the dystrophin-glycoprotein complex can be isolated as an intact complex with lectins that bind to the glycoprotein components of the complex. The lectins are typically coupled to a solid support such as a chromatographic gel (i.e., sepharose, agarose, etc.) and a complex mixture of membrane components is passed through a chromatography column containing the gel with bound lectin. The glycoproteins of membrane components bind to the lectin while the other components of the mixture pass through the column. It has been discovered that one of the components of the dystrophin-glycoprotein complex binds to the lectin, wheat germ agglutinin (WGA). Thus, WGA can be used coupled to a chromatographic gel such as sepharose (see Example I for greater detail) to isolate the dystrophin-glycoprotein complex.

The dystrophin-glycoprotein complex can be further purified using density gradient ultracentrifugation. The eluate from the affinity column as described above is applied as a narrow band to the top of a solution in a centrifuge tube. To stabilize the sedimenting components of the eluate against convection mixing, the solution beneath the band contains an increasing dense solution of an inert, highly soluble material such as sucrose (a density gradient). Under these conditions, the different fractions of the eluate sediment at different rates forming distinct bands that can be individually collected. The rate at which each component sediments depends on its size and shape and is normally expressed as its sedimentation coefficient or S value.

Present day ultracentrifuges rotate at speeds up to about 80,000 rpm and produce forces up to about $500,000\times$ gravity. At these enormous forces, even relatively small macromolecules, such as tRNA molecules and simple enzymes, separate from one another on the basis of their size. Using this technique, the size of the dystrophin-glycoprotein complex was estimated to be approximately 18 S by comparing its migration to that of standards of varying size.

Another form of affinity chromatography which can be used to isolate the dystrophin-glycoprotein complex is known as immunoaffinity purification. This technique utilizes the unique high specificity of antibodies both polyclonal and monoclonal. Antibodies are extremely valuable tools for rapid, selective purification of antigens. In principle, the antigen is coupled (immobilized) on a column support and this is used to selectively adsorb antigen from a mixture containing many other antigens. The antigens for which the antibody has no affinity can be washed away, and the purified antigen then eluted from its high affinity antibody with an elution buffer. In the present invention, monoclonal antibodies XIXC2 and $IVD3_1$ can be used as the antibodies which are coupled to the column support and thus used for isolating the dystrophin-glycoprotein complex using immunoaffinity chromatography (see Example III for specific detail).

The separation and isolation of the components of the dystrophin-glycoprotein complex can be accomplished by SDS-polyacrylamide gel electrophoresis (SDS-PAGE). In this technique, proteins are reacted with the anionic detergent, sodium dodecylsulfate (SDS or sodium laurylsulfate), to form negative charged complexes. The amount of SDS bound by a protein, and so the charge on the complex, is roughly proportional to its size. Commonly, about 1.4 grams SDS is bound per 1 gram protein, although there are exceptions to this rule. The proteins are generally denatured and solubilized by their binding of SDS, and the complex forms a prolate elipsoid or rod of a length roughly proportionate to the proteins' molecular weight. Thus, proteins of either acidic or basic isoelectric point form negative charged complexes that can be separated on the basis of differences in charges and sizes by electrophoresis through a sieve-like matrix of polyacrylamide gel. One who is skilled in the art of SDS-PAGE can routinely separate the components of the dystrophin-glycoprotein complex that was isolated by sucrose gradient ultracentrifugation or immunoaffinity chromatography by using this method (see Example I and FIG. 4).

An alternative method for isolating the components of the dystrophin-glycoprotein complex is gel filtration high pressure liquid chromatography. This technique, in addition to taking less time than SDS gel electrophoresis, allows easier quantitation and recovery of separated proteins, and the resolution is better than that achieved by gel filtration with conventional materials.

The volume accessible to a protein in gel filtration supports depends on its size and shape. Thus, in order to determine molecular weight the sample protein must have the same shape as the proteins used for calibration. In the presence of denaturents such as sodium dodecyl-sulfate, all proteins in their reduced state adopt a linear random coil confirmation whose molecular radius is proportional to molecular weight. Under these conditions, the molecular weight of a protein can be expressed in terms of its elution volume from the column.

Denaturation causes an increase in the intrinsic viscosity of the protein, and hence an increase in the molecular dimensions. Thus, under denaturing conditions, the molecular weight exclusion limits of gel filtration matrices are lower than those in the absence of denaturement. Of the column supports used for HPLC gel filtration under denaturing conditions, those of the TSK-G-3000 SW Type are suitable for proteins of less than 70,000 molecular weight, whereas the TSK-Go4000 SW Type can be used for proteins up to 60,000 molecular weight. One who is skilled in the art of gel filtration, high pressure liquid chromatography can easily separate the components of the dystrophin-glycoprotein complex following isolation by sucrose gradient ultracentrifugation or immunoaffinity chromatography.

Monoclonal and polyclonal antibodies specific for non-dystrophin components of the dystrophin-glycoprotein complex are particularly useful in the isolation and diagnostic methods of this invention. Monoclonal antibodies useful in this invention are obtained by well-known hybridoma methods. An animal is immunized with a preparation containing the dystrophin-glycoprotein complex. A fused cell hybrid is then formed between antibody-producing cells from the immunized animal and an immortalizing cell such as a myeloma.

In preferred embodiments, anti-non-dystrophin component monoclonal antibodies of this invention are produced by murine hybridomas formed by fusion of: a) mouse myeloma or hybridoma which does not secrete antibody with b) murine spleen cells which secrete antibodies obtained from mice immunized against dystrophin-glycoprotein complex.

Typically, the mice are immunized with a primary injection of dystrophin-glycoprotein complex followed by a number of boosting injections of dystrophin-glycoprotein complex. During or after the immunization procedure, sera of the mice may be screened to identify those mice in which a substantial immune response to the complex has been evoked. From selected mice, the spleen cells are obtained and fusions are performed. Suitable fusion techniques are the Sendai virus technique (Köhler, G. and Milstein, C., *Nature*, 256: 495 (1975), or the polyethylene glycol method (Kennet, R. H., "Monoclonal Antibodies, Hybridomas— A New Dimension in Biological Analysis", Eds. R. H. Kennet, T. J. McKern and K. B. Bechtol, Plenum Press, N.Y. (1980)).

The hybridomas are then screened for production of anti-non-dystrophin component antibodies. A suitable screening technique is a solid phase radio-immunoassay. A solid phase immunoadsorbent is prepared by coupling dystrophin-glycoprotein complex or non-dystrophin components to an insoluble matrix. The immunoadsorbent is brought into contact with culture supernatants of hybridomas. After a period of incubation, the solid phase is separated from the supernatants, then contacted with a labeled antibody against murine immunoglobulin. Label associated with the immunoadsorbent indicates the presence of hybridoma products reactive with dystrophin-glycoprotein complexes or non-dystrophin components. The hybridoma products are then examined for their ability to react with natural and synthetic components of the dystrophin-glycoprotein complex.

The monoclonal anti-non-dystrophin component antibodies can be produced in large quantities by injecting anti-non-dystrophin component antibody producing hybridoma cells into the peritoneal cavity of mice and, after an appropriate time, harvesting acites fluid from the mice which yield a high titer of homogenous antibody. The monoclonal antibodies are isolated therefrom. Alternatively, the antibodies can be produced by culturing anti-non-dystrophin component antibody producing cells in vitro and isolating secreted monoclonal anti-non-dystrophin component antibodies from the cell culture medium directly.

Another method of forming antibody-producing cells is by viral or oncogenic transformation. For example, a B-lymphocyte which produced a non-dystrophin component specific antibody may be infected and transformed with a virus, such as the Epstein-Barr virus, to give an immortal antibody-producing cell. See Kozbon and Roder, *Immunology Today*, 4(3): 72–79 (1983). Alternatively, the B-lymphocyte may be transformed by a transforming gene or gene product.

Polyclonal antibodies can be prepared by immunizing an animal with a crude preparation of the dystrophin-glycoprotein complex or the purified non-dystrophin components of the complex as illustrated in FIGS. 2 and 3, respectively. The animal is maintained under conditions whereby antibodies reactive with the components of the complex are produced. Blood is collected from the animal upon reaching a desired titer of antibodies. The serum containing the polyclonal antibodies (antisera) is separated from the other blood components. The polyclonal antibody-containing serum can optionally be further separated into fractions of particular types of antibodies (e.g., IgG or IgM).

In the preferred embodiment of the diagnostic method of the invention, a muscle biopsy sample is treated in a procedure which renders the non-dystrophin components available for complexing with antibodies directed against said components. The complexes of antibody and non-dystrophin components are detected and the levels of detection between normal samples and patient samples are compared.

Muscle samples are obtained from patients by surgical biopsy. The site of biopsy could be any skeletal muscle suspected of being dystrophic. Muscle groups about the shoulder and pelvic girdles, however, are the most affected, and are likely to be the most common site of biopsy. The amount of muscle obtained should be enough to extract the components of the dystrophin-glycoprotein complex from muscle membranes and detect their presence by the diagnostic methods described within this application. Alternative methods of extraction can be used.

For biopsy samples greater than 500 mg, the muscle tissue can be homogenized by mechanical disruption using apparatus such as a hand operated or motor driven glass homogenizer, a Warning blade blender homogenizer, or an ultrasonic probe. Homogenization can occur in a buffer comprising 20 mM sodium pyrophosphate, 20 mM sodium phosphate monohydrate, 1 mM magnesium chloride, 0.303M sucrose, 0.5 mM EDTA, pH 7.1, with various protease inhibitors such as aprotinin (0.5 μg/ml), benzamidine (100 μg/ml), iodoacetamide (185 μg/ml), leupeptin (0.5 μg/ml), pepstatin A (0.5 μg/ml) and PMSF (40 μg/ml). Heavy microsomes can be prepared from homogenized skeletal muscle by the method of Mittchel, et al., *J. of Cell Biol.*, 95: 1008–1016 (1983). The microsomes are then washed with a physiological salt solution and solublized in saline containing detergent and protease inhibitors. Following solubilization of the microsomes, the sample is treated with sodium dodecylsulfate (SDS). In the present case, SDS acts to dissociate the linked components of the dystrophin-glycoprotein complex, thereby allowing their separation.

For muscle biopsy samples less than 500 mg, the extraction procedure described in Example V can be used. Samples are frozen in liquid nitrogen and crushed using a mortar and pestle and prepared for electrophoresis by treatment with SDS as described by Hoffman, et al., *N. Eng. J. of Med.*, 318: 1363–1368 (1988), hereby incorporated by reference.

The SDS treated sample is then electrophoresed by polyacrylamide gel electrophoresis (PAGE). The sample is introduced to the electrophoretic system at the stacking gel. With an electric field applied, ions move toward electrodes, but at the pH prevailing in the stacking gel, the protein-SDS complexes have mobilities intermediate between chloride ions (present throughout the system) and glycinate ions (present in the reservoir buffer). The chloride ions have the greatest mobility. The following larger ions concentrate into narrow zones in the stacking gel, but are not effectively separated there. When the moving zones reach the separating gel, their respective mobilities change in the pH prevailing there and the glycinate ion front overtakes the protein-SDS complex zones to leave them in a uniformly buffered electric field to separate from each other according to size and charge. Since protein (or rather their complexes with SDS) are resolved largely on the basis of differences in their sizes, electrophoretic mobility in SDS gels may be used to estimate the molecular weight of a protein by comparison of proteins of known size.

Following separation by SDS-PAGE, the separated components of the dystrophin-glycoprotein complex are transferred from the gel matrix to another support. The components are transferred out of the gel and onto a filter or membrane, forming an exact replica of the original protein separation, but leaving the transferred proteins accessible for further study. This transfer is known as protein blotting. There are two common methods for blotting, electroblotting and passive diffusion blotting. The support matrices that can be used in the transfer include nitrocellulose filters, nylon filters, diazo papers, diethylaminoethyl (DEAE), anion exchange papers and membranes. The detection of transferred proteins can be accomplished by the use of general protein dyes such as Amido black or Coomassie brilliant blue. Alternatively, antibodies which are specific for the known non-dystrophin components of the dystrophin-glycoprotein complex can be used to bind to the various components. The complexes of antibodies and nondystrophin components can be detected with labeled antibodies. The levels of detection between normal samples and samples suspected of being extracted from muscle affected by muscular dystrophy are compared. Samples with lower detection than normal are considered to be extracted from dystrophic muscle.

Human tissue specimens (e.g., biopsy samples) can be tested for the presence of the components of the dystrophin-glycoprotein complex by using monoclonal or polyclonal antibodies in an immunohistochemical technique, such as the immunoperoxidase staining procedure. Alternatively, immunofluorescent techniques can be used to examine human tissue specimens. In a typical protocol, slides containing cryostat sections of frozen, unfixed tissue biopsy samples are air-dried and then incubated with the anti-non-dystrophin component antibody preparation in a humidified chamber at room temperature. The slides are layered with a preparation of fluorescently labeled antibody directed against the monoclonal antibody. The staining pattern and intensities within the sample are determined by fluorescent light microscopy.

The antibodies of the present invention can also be used in an enzyme-linked immunosorbant assay (ELISA) for determining the absence or presence of non-dystrophin components of the dystrophin-glycoprotein complex. Antibodies against non-dystrophin components to be measured are adsorbed to a solid support, in most cases a polystyrene microtiter plate. After coating the support with antibody and washing, a solubilized sample is added. If a non-dystrophin component is present for which the antibodies are specific, they will bind to the adsorbed antibodies. Next, a conjugate that will also bind to the non-dystrophin component is added. Conjugates are secondary antibody molecules to which an enzyme is covalently bound. After addition of a chromogenic substrate for the enzyme, the intensity of the colored reaction products generated will be proportional to the amount of conjugated enzyme and thus indirectly to the amount of bound non-dystrophin component. Since the intensity of the developed color is proportional to the amount of non-dystrophin component present, determination of the intensity of the color produced by a standard series of non-dystrophin component concentrations will allow the calculation of the amount of non-dystrophin component in an unknown sample. Many variations of this assay exist as described in Voller, A., Bidwell, D. E. and Bartlett, A., The Enzyme Linked Immunosorbent Assay (ELISA): A guide with abstracts of microplate applications, Dynatech Laboratories, Alexandria, Va. (1979) and are hereby incorporated by reference.

The invention is now further and specifically illustrated by the following examples. All parts and percentages are by weight unless otherwise specified.

EXAMPLE I

Sedimentation of dystrophin-glycoprotein complex through 5% to 20% linear sucrose gradients Heavy microsomes were prepared from rabbit skeletal muscle by the method described in Mitchell, et al., *J. of Cell Bio.*, 95: 1008–1016 (1983). The teachings of all scientific publications cited in all examples herein are hereby incorporated by reference. The microsomes were washed twice with 0.6M KCl in 50 mM tris-HCl, pH 7.4, 0.165M sucrose, 0.1 mM PMSF and 0.75 mM benzamidine to remove contractile proteins. One gram of KCl-washed membranes were solubilized in 1.0% digitonin, 0.5M NaCl, and protease inhibitors as previously described in Campbell, K. P. and Kahl, S. D., *Nature*, 338: 259–262 (1989). After removal of the ryanodine receptor by immunoaffinity chromatography as described in Imagawa, T., et al., *J. of Biol. Chem.*, 262:

16636-16643 (1987), the digitonin-solubilized membranes were circulated overnight in a 40 ml WGA-sepharose column, washed extensively, then eluted with three column volumes of 0.3M N-acetyl-glucosamine. Eluted fractions containing dystrophin were applied to a 3 ml DEAE cellulose column and sequentially eluted with the following NaCl concentrations in buffer A (0.1% digitonin, 50 mM tris-HCL, pH 7.4, 0.75 mM benzemidine, 0.1 mM PMSF): 0 mM, 25 mM, 50 mM, 75 mM, 100 mM, 110 mM and 175 mM. Sucrose gradients (12.5 ml linear 5% to 20% sucrose) containing 0.5M NaCl and 0.01% $NaN_3$ in buffer A were prepared using a Beckman density gradient former. Dystrophin-glycoprotein complex, which eluted in fraction two (3 ml) from the DEAE-column 175 mM NaCl wash was concentrated to 0.5 ml in a centricon-100 (Amicon), layered on a sucrose gradient, and overlaid with 0.5 ml of buffer A containing 175 mM NaCl and 0.01% $NaN_3$. Gradients were centrifuged at 4° C in a Beckman VTi 65.1 vertical rotor for 90 minutes at 200,000XG. Fractions (0.6 ml) were collected from the top of the gradients using an ISCO Model 640 density gradient fractionator. Gradient fractions were separated by SDS-PAGE (3% to 12% gradient gel) and 'stained with Coomassie Blue (300 ul of fractions concentrated to 50 ul with a centricon-100) or transferred to nitrocellulose (75 ul of fractions in B, 25 ul in C and D, and 50 ul in E and F) and stained with various antibodies. The blot shown in (E) was prepared from a gel run in the absence of reducing agent plus 10 mM N-ethyl-maleimide. Gel lanes were scanned with a Hoefer GS300 scanning densitometer and analyzed using GS-360 data analysis software. Polyclonal antisera against a chemically synthesized decapeptide representing the C-terminal of dystrophin was raised in New Zealand white rabbits as previously described in Strynadka, N. C. J., et al., *J. of Virol.*, 62: 3474-3483 (1988). Hybridomas were obtained from female balb/C mice which were immunized with rabbit skeletal muscle membranes and boosted with WGA eluate as described in Jorgensen, A. O., et al., *Cell Motility and Cytoskeleton*, 9: 164-174 (1988).

It was evident from the Coomassie Blue-stained gel of sequential gradient fractions (FIG. 4a) that the dystrophin-glycoprotein complex was clearly separated from the voltage-sensitive sodium channel and the dihydropyridine receptor (FIG. 4). The size of the dystrophin-glycoprotein complex was estimated to be approximately 18 S by comparing its migration to that of the standards B-galactosidase (15.9 S), thyroglobulin (19.2 S) and the dihydropyridine receptor (20 S). Densitometric scanning of the peak dystrophin-glycoprotein containing gradient fractions (fractions 10 and 11 in FIG. 4a) revealed several proteins which copurified with dystrophin: a broad, diffusly staining component with an apparent $M_r$ of 156 kDa, 88kDa protein, a triplet of proteins centered at 59 kDa, 50 kDa protein, a protein doublet at 43 kDa, 35 kDa protein and a 25 kDa protein.

Figure 4B:
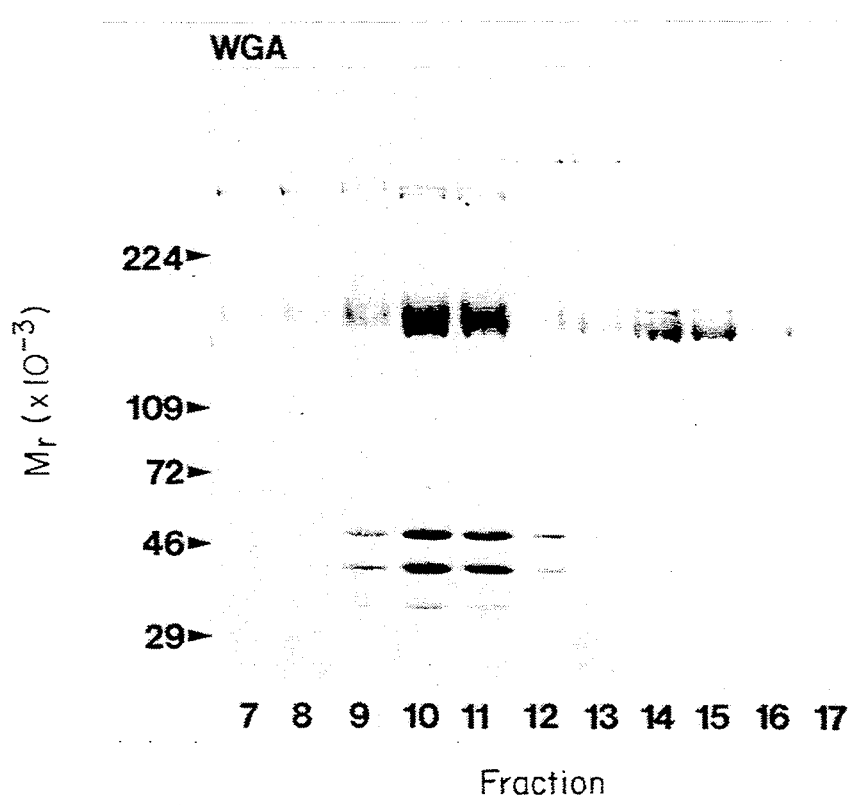

In order to identify the glycoprotein constituents of the dystrophin-glycoprotein complex, sucrose gradient fractions 7-17 were electrophoretically separated, transferred to nitrocellulose, and stained with peroxidase-conjugated WGA (FIG. 4b). Four WGA-binding proteins with apparent $M_r$ of 156 k, 50 k, 43 k and 35 k were found to strictly copurify with dystrophin. All four of the WGA-binding proteins were also stained with peroxidase-conjugated concanavalin A. In addition, the lower $M_r$ component of the 43 kDa protein doublet, apparent with Coomassie Blue staining (FIG. 4a), was also stained with concanavalin A.

Figure 4C:
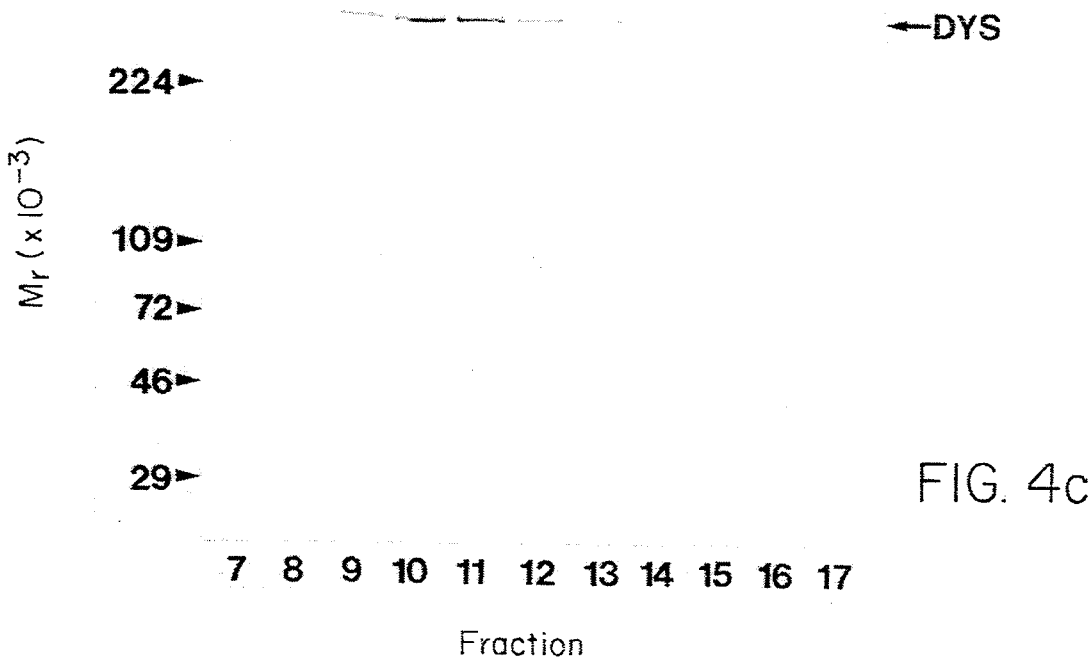
Figure 4D:
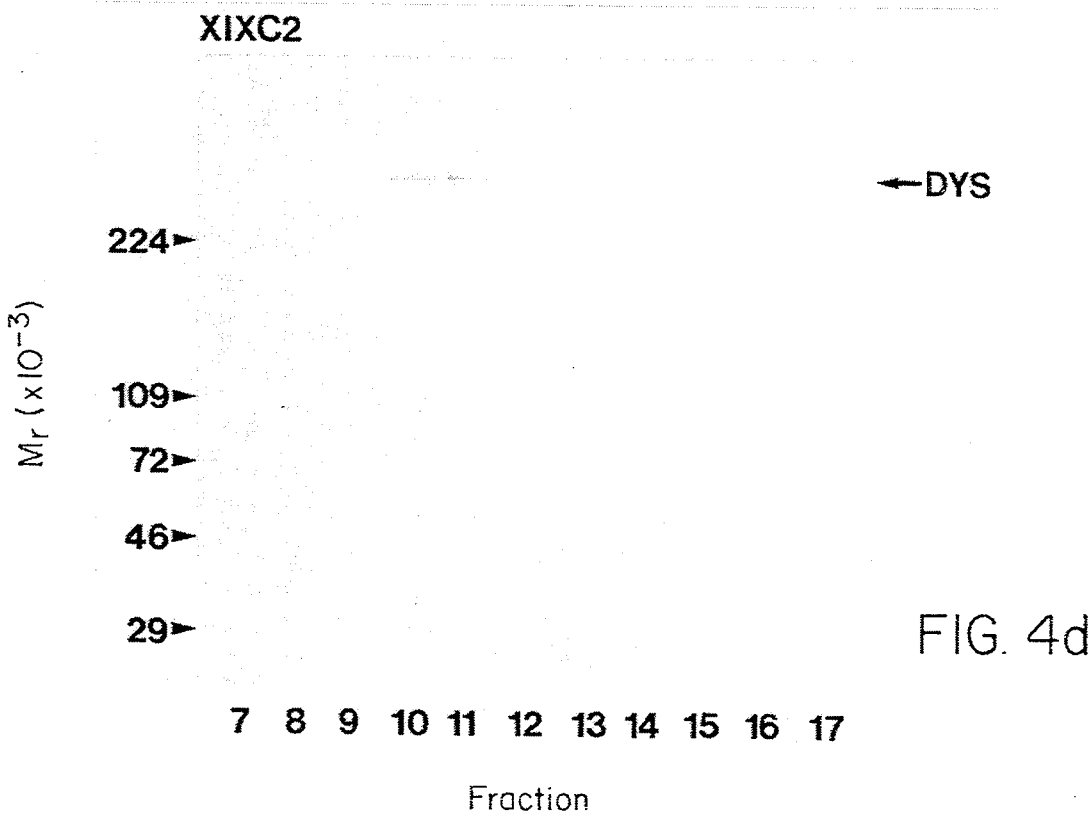

The dystrophin-glycoprotein complex was further characterized with antibodies raised against various components of the complex. Antisera from a rabbit which was immunized with a chemically synthesized stain a single $M_r$ protein as seen in FIG. 4c. This decapeptide representing the predicted C-terminal amino acid sequence of human dystrophin was found to protein comigrated with the predominant isoform of dystrophin stained by sheep polyclonal anti-dystrophin antibodies.

A library of monoclonal antibodies against muscle proteins eluted from WGA-sepharose was also screened for reactivity against components of the dystrophin-glycoprotein complex. Of six hybaidomas which showed immunofluorescence staining only on the sarcolemma (see Example II), monoclonal antibodies XIXC2 (FIG. 4d) and VIA42 were found to stain dystrophin on immunoblots. Both dystrophin monoclonal antibodies recognized the minor lower $M_r$ isoform of dystrophin are IgM subtypes, and recognized both native and denatured dystrophin. Monoclonal antibody XIXC2 also which appears to copurify with the more abundant isoform seen in FIG. 4d.

Two of the other sarcolemma-specific monoclonal antibodies were specific for components of the dystrophin-glycoprotein complex (FIGS. 4e and 4f). The 50 kDa glycoprotein stained with monoclonal antibody $IVD3_1$ as seen in FIG. 4e. Monoclonal $IVD3_1$ recognized only the nonreduced form of the 50 kDa glycoprotein and it is not highly crossreactive. Monoclonal antibody $VIA4_1$ stained the 156 kDa glycoprotein as seen in FIG. 4f which copurified with dystrophin. Monoclonal antibody $VIA4_1$ recognized the denatured form of the 156 kDa glycoprotein and is highly crossreactive.

EXAMPLE II

Immunolocalization of components of the dystrophin-glycoprotein complex

The indirect immunofluorescence labeling of fixed 8 μm transverse cryostat sections from rabbit gastrocnemious was carried out as described in Jorgensen, A. O., et al., op. cit. Sections were preincubated for 20 minutes with 5% normal goat antiserum in phosphate buffered saline, followed by a two hour incubation at 37° C. with the primary antibody (hybridoma supernatants or 1:1000 diluted antiserum). After washing in PBS, the sections were further incubated for 30 minutes at 37° C. in PBS with a 1:50 dilution of FITC-labeled goat F(ab')2 anti-mouse IgG or anti-rabbit IgG and subsequently examined in a Leitz fluorescence microscope. Staining of cryostat sections was not observed with non-immunue serum, nor was there any nonspecific binding to the tissue by fluorescein-labeled secondary antibody.

Figure 5A:
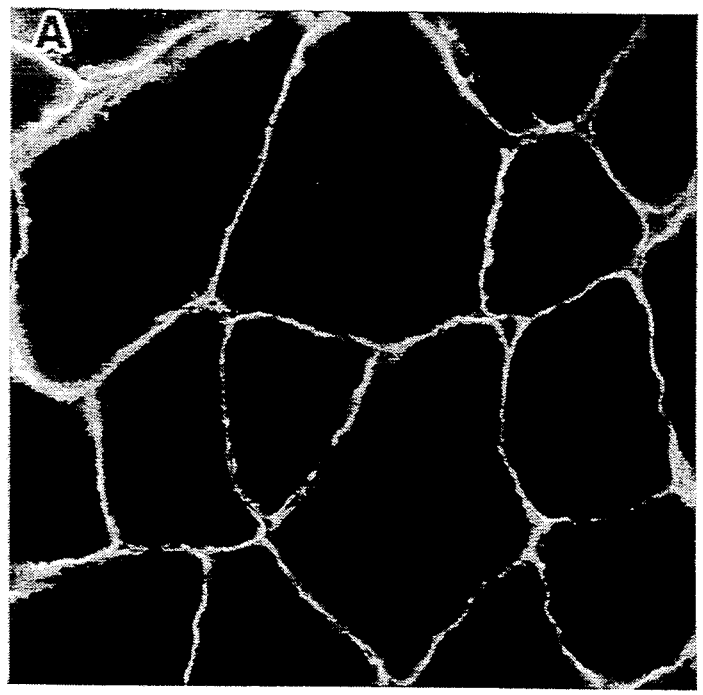
FIG. 5 a, b, c and d depict the immunolocalization of the components of the dystrophin-glycoprotein complex in transverse cryostat sections of rabbit skeletal muscle (magnification=250X).
Figure 5B:
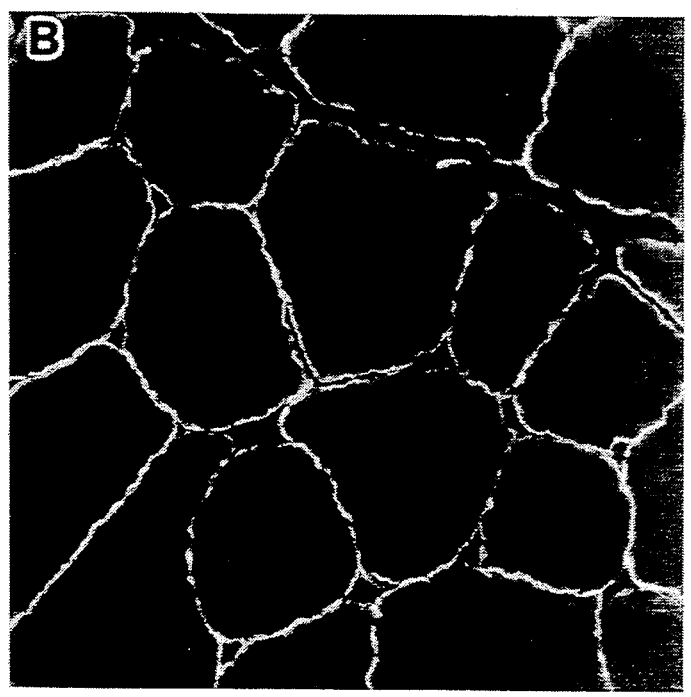
Figure 5C:
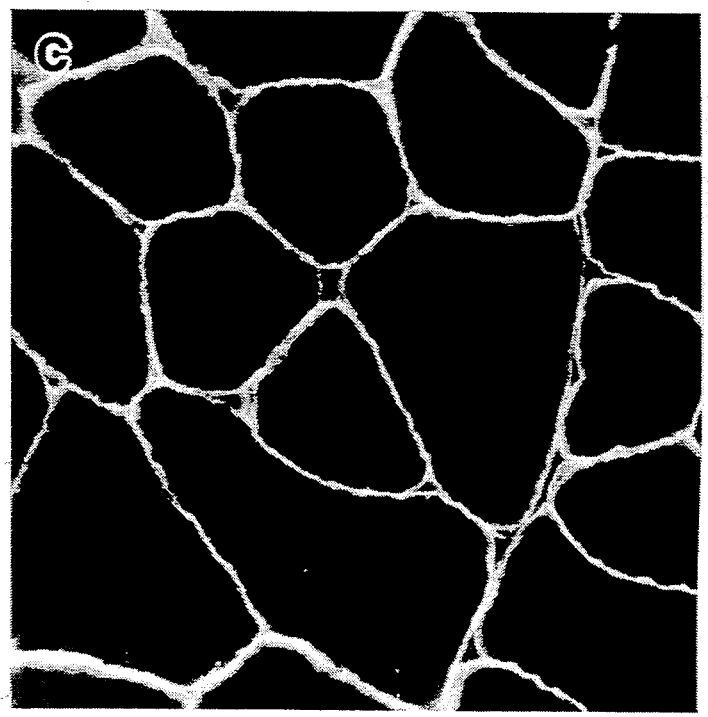
Figure 5D:

The antisera to the C-terminal amino acid sequence of human dystrophin showed immunofluorescence staining only on the cell periphery as seen in FIG. 5a, which indicates a restricted localization of dystrophin to the sarcolemma of rabbit skeletal muscle. This observation was confirmed by staining rabbit skeletal muscle with monoclonal antibody XIXC2 against dystrophin and, again, localization was observed in the sarcolemma of the rabbit skeletal muscle. The 50 kDa glycoprotein stained with monoclonal $IVD3_1$, as seen in FIG. 5c, has been localized exclusively to the sarcolemmal membrane of rabbit skeletal muscle. Monoclonal antibody VIA4$_1$ exhibited weak, but specific, immunofluorescent staining of the sarcolemmal membrane as seen in FIG. 5d, consistent with its low affinity for the native 156 kDa glycoprotein. In agreement with immunofluorescence results, a rabbit membrane preparation greatly enriched in sarcolemmal proteins also exhibits a substantial enrichment in dystrophin, the 156 kDa and 50 kDa glycoproteins. Immunofluorescence staining for dystrophin, 50 kDa glycoprotein or the 156 kDa glycoprotein was equally distributed in fast and slow muscle fibers.

EXAMPLE III

Immunoadsorption of the dystrophin-glycoprotein complex

Immunoaffinity beads prepared as described in Campbell, K. P., et al., *J. of Biol. Chem.*, 262: 6460–6463 (1987), were equilibrated with buffer A containing 0.5M NaCl and then incubated overnight (12 hours) with 0.75 ml of fraction 2 from the 1.75 mM NaCl wash of the DEAE-cellulose column as described in Example I. After pelleting, the supernatants were decanted (voids) and the affinity beads were washed with 5×0.7 ml aliquots of buffer A containing 0.5M NaCl. The void from each affinity column and the five washes were pooled and concentrated to 375 ul in a centricon 100 (Amicon). In addition, 0.75 ml of fraction 2 was diluted to 4.2 ml with buffer A, concentrated to 375 ul and used as control. Column voids were analyzed by SDS-PAGE and immunoblotted as described in Example I.

The voids from the XIXC2 (anti-dystrophin) and the IVD3$_1$ (anti-50 kDA glycoprotein) immunoaffinity beads contained no dystrophin, 59 kDa triplet, 50 kDa glycoprotein, 43 kDa doublet or 35 kDa proteins as detected by Coomassie Blue staining. It is apparent from FIG. 6b that both the XIXC2 (anti- dystrophin) and IVD31 (anti-50 kDA glycoprotein) immunoaffinity beads quantitatively removed dystrophin from the starting material. Analysis of the voids for the 156 kDa glycoprotein, as seen in FIG. 6c, and the 50 kDa glycoprotein, as seen in FIG. 6d, revealed that both the XIXC2 and the IVD3$_1$ immunoaffinity beads selectively adsorbed all but a trace of each of these glycoproteins from the voids while the voltage-sensitive sodium channel, as seen in FIG. 6a, and the alpha$_1$ and alpha$_2$ subunits of the dihydropyridine receptor remained in the voids. As detected by peroxidase-conjugated WGA, the 43 kDa and 35 kDa glycoproteins were also adsorbed from the voids. Immunoblots of immunoaffinity beads separated on gels indicated that dystrophin, the 156 kDa and 50 kDa glycoproteins were retained by the beads and not selectively proteolyzed. Initial experiments with monoclonal VIA4$_1$ (anti-156 kDa glycoprotein) have indicated that it has too low an affinity for the native 156 kDa glycoprotein to be successful in this type of an experiment.

Example IV

Immunoblot analysis of control and dystrophic mouse muscle membranes

Membranes from control and dystrophic mice (mdx) were prepared in 10% sucrose, 76.8 mM aprotinin, 0.83 mM benzamidine, 1 mM iodoacetamide, 1.1 uM leupeptin, 0.7 uM pepstatin A, 0.23 mM PMSF, 20 mM tris-maleate, pH 7.0, by centrifuging muscle homogenates for 15 minutes for 14,000 XG and subsequently pelleting the supernatant for 30 minutes at 125,000×g followed by KCl washing as described in Example I. Control and dystrophic mouse muscle membranes were analyzed by SDS-PAGE and immunoblotting as described in Example I. The amount of 156 kDa glycoprotein in each preparation was estimated densitometrically from autoradiographs of identical blots incubated with $^{125}$I-labeled sheep anti-mouse secondary antibody.

Staining with polyclonal antisera against the C-terminal decapeptide of dystrophin revealed that dystrophin was completely absent from dystrophic mouse membranes as seen in FIG. 7a. In addition, comparison of normal and dystrophic mouse with immunostaining by monoclonal antibody VIA4$_1$ against the 156 kDa glycoprotein revealed that the 156 kDa glycoprotein was absent or greatly reduced in dystrophic mouse membranes as observed in FIG. 7b. Staining of identical transfers with sheep polyclonal antisera against either the ryanodine receptor, seen in FIG. 7c, or the dihydropyridine receptor, as seen in FIG. 7d, did not differ between control and dystrophic mouse muscle membranes. Monoclonal antibody IVD3$_1$ against the 50 kDa glycoprotein did not crossreact with normal mouse membranes and, thus, could not be evaluated. The absence of the 156 kDa glycoprotein was also confirmed using SDS muscle extracts instead of isolated membranes from control and dystrophic mice. Estimation of the 156 kDa glycoprotein remaining in the dystrophic muscle membranes using $^{125}$I-labeled secondary antibodies and total membrane preparations from four different control and four different dystrophic mice revealed an average reduction of 85% in dystrophic muscle.

EXAMPLE V

Immunoblot analysis of normal and human muscle biopsies

Frozen muscle biopsy samples (50 mg) were crushed in liquid nitrogen using a mortar and a pestle and then prepared for electrophoresis as described by Hoffman, et al., *N. Eng. J. of Med.*, 318: 1363–1368 (1988). The pulverized muscle samples were transferred to ten volumes of SDS-PAGE sample buffer (10% SDS, 2M sucrose, 4% 2-mercaptoethanol, 0.002% bromophenyl blue, 260 mM tris-HCl, pH 6.8), vortexed, and precipitated material allowed to settle. Aliquots (50 ul) of the SDS-extracted muscle samples were analyzed by SDS-PAGE and immunoblotting as described in Example I and the amount of 156 kDa glycoprotein was estimated as described in Example IV.

The dystrophic samples exhibited no staining with antibodies against dystrophin by indirect immunofluorescence microscopy and immunoblotting as seen in FIG. 8a. In contrast to the normal muscle extract, the 3 DMD samples showed greatly reduced staining for the 156 kDa glycoprotein as observed in FIG. 8b. On the other hand, identical immunoblots stained with monoclonal antibodies against the $Ca^{2+}$ dependent ATPase as seen in FIG. 8c revealed no difference in the staining intensity between normal and dystrophic muscle samples. Again, the amount of 156 kDa glycoprotein was estimated to be reduced by approximately 90% in DMD samples.

Equivalents

Those skilled in the art will recognize, or be able to ascertain using no more than routine experimentation, many equivalents to the specific embodiment of the invention described specifically herein. Such equivalents are intended to be encompassed in the scope of the following claims.

We claim:

1. A method for identifying a substantial reduction in the amount of a component of a mammalian dystrophin-glycoprotein complex from an experimental mammalian muscle tissue sample, relative to a standard muscle tissue sample, the method comprising:
   a) combining the experimental sample, previously treated to render the non-dystrophin components available for antibody binding, with a substantially pure polyclonal antibody preparation which specifically binds to a non-dystrophin component consisting essentially of a glycoprotein having a molecular weight of about 156 kDa;
   b) detecting and characterizing the extent of the binding of the polyclonal antibodies to the non-dystrophin component having a molecular weight of about 156 kDa; and
   c) comparing the extent of binding to the sample with the extent of binding to a standard muscle tissue sample treated as described in steps a) and b).

2. A method of claim 1, wherein the substantially pure polyclonal antibody preparation is affinity purified from polyclonal antisera.

3. A method for identifying a substantial reduction in the amount of a component of a mammalian dystrophin-glycoprotein complex from an experimental mammalian muscle tissue sample, relative to a standard muscle tissue sample, the method comprising:
   a) combining the experimental sample, previously treated to render the non-dystrophin components available for antibody binding, with a substantially pure preparation of a monoclonal antibody which specifically binds to a non-dystrophin component of the dystrophin-glycoprotein complex consisting essentially of a glycoprotein having a molecular weight of about 156 kDa;
   b) detecting and characterizing the extent of the binding of the monoclonal antibody to the non-dystrophin component having a molecular weight of about 156 kDa; and
   c) comparing the extent of binding to the sample with the extent of binding to a standard muscle tissue sample treated as described in steps a) and b).

4. A substantially pure polyclonal antibody preparation which specifically binds to a non-dystrophin component of the mammalian dystrophin-glycoprotein complex wherein said non-dystrophin component is a glycoprotein having a molecular weight of about 156 kDa.

5. The substantially pure polyclonal antibody preparation of claim 4, which is affinity purified.

6. A monoclonal antibody which specifically binds to a non-dystrophin component of the mammalian dystrophin-glycoprotein complex wherein said non-dystrophin component is a glycoprotein having a molecular weight of about 156 kDa.

7. A hybridoma which produces a monoclonal antibody which specifically binds to a non-dystrophin component of the mammalian dystrophin-glycoprotein complex wherein said non-dystrophin component is a glycoprotein having a molecular weight of about 156 kDa.

* * * * *